US007177683B2

(12) United States Patent
Belk (10) Patent No.: US 7,177,683 B2
(45) Date of Patent: Feb. 13, 2007

(54) HISTORY-DEPENDENT PACING INTERVAL DETERMINATION FOR ANTITACHYCARDIA PACING

(75) Inventor: Paul Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 586 days.

(21) Appl. No.: 10/426,397

(22) Filed: Apr. 30, 2003

(65) Prior Publication Data

US 2004/0220634 A1 Nov. 4, 2004

(51) Int. Cl.
*A61N 1/365* (2006.01)

(52) U.S. Cl. .......................................... 607/14; 607/25

(58) Field of Classification Search ...................... None
See application file for complete search history.

(56) References Cited

U.S. PATENT DOCUMENTS

| 4,280,502 A | 7/1981 | Baker, Jr. et al. ..... 128/419 PG |
| 4,577,633 A | 3/1986 | Berkovits et al. ..... 128/419 PG |
| 4,587,970 A | 5/1986 | Holley et al. ......... 128/419 PG |
| 4,593,695 A * | 6/1986 | Wittkampf ................... 607/27 |
| 4,880,005 A | 11/1989 | Pless et al. ........... 128/419 PG |
| 4,998,974 A | 3/1991 | Aker |
| 5,342,404 A | 8/1994 | Alt et al. |
| 5,454,836 A | 10/1995 | Van der Veen et al. |
| 5,782,887 A * | 7/1998 | van Krieken et al. ......... 607/25 |
| 5,871,511 A | 2/1999 | Bolz et al. |
| 5,882,352 A | 3/1999 | Duncan et al. |
| 6,058,328 A | 5/2000 | Levine et al. |
| 6,064,907 A | 5/2000 | Thong et al. |
| 6,129,745 A | 10/2000 | Sun et al. |
| 6,360,126 B1 | 3/2002 | Mika et al. ..................... 607/9 |
| 6,361,503 B1 * | 3/2002 | Starobin et al. ............ 600/508 |
| 6,400,986 B1 | 6/2002 | Sun et al. |
| 6,445,949 B1 | 9/2002 | Kroll |
| 6,466,819 B1 | 10/2002 | Weiss ............................. 607/5 |
| 6,920,353 B1 * | 7/2005 | Heinze et al. .................. 607/5 |
| 2003/0060724 A1 | 3/2003 | Thiagarajan et al. ........ 600/515 |
| 2004/0015088 A1 * | 1/2004 | Gray et al. .................. 600/509 |

OTHER PUBLICATIONS

U.S. Appl. No. 10/260,845, filed Sep. 30, 2002.
Franz, M.R., et al., "Cycle Length Dependence of Human Action Potential Duration in Vivo. Effects of Single Extrastimuli, Sudden Sustained Rate Acceleration and Deceleration and Different Steady-State Frequencies", *Journal Clinical Invest*, 1988; 82:972-9.

* cited by examiner

*Primary Examiner*—Kristen Mullen
(74) *Attorney, Agent, or Firm*—Michael C. Soldner; Girma Wolde-Michael (57) ABSTRACT

A method and device for delivering anti-tachycardia pacing pulses that may be used to treat episodes of atrial or ventricular tachycardia. Episodes of atrial or ventricular tachycardia can occur while the heart is at a normal rhythm or an accelerated rhythm. The method and device is directed to determining an estimate of action potential duration of a heart that experiences episodes of atrial or ventricular tachycardia for use in determining a pacing interval for anti-tachycardia pacing pulses that may more effectively terminate the tachycardia.

26 Claims, 7 Drawing Sheets

HISTORY-DEPENDENT PACING INTERVAL DETERMINATION FOR ANTITACHYCARDIA PACING

TECHNICAL FIELD

The invention relates to implantable medical devices, and more particularly, to implantable medical devices for treating episodes of tachycardia.

BACKGROUND

An arrhythmia is a disturbance in the normal rate, rhythm or conduction of the heartbeat. A ventricular arrhythmia originates in the ventricles. Ventricular tachycardia (VT), one form of ventricular arrhythmia, is a condition in which the ventricles contract at a high rate, e.g., 110 or more beats per minute. Ventricular fibrillation (VF), another form of ventricular arrhythmia, is characterized by a chaotic and turbulent activation of ventricular wall tissue. The number of depolarizations per minute during VF can exceed 400.

VT can lead to VF, which in turn can be life threatening. VT is also associated with other low cardiac output symptoms, such as fatigue. Many VTs are episodic, marked by abrupt onset but also abrupt termination, but cause considerable patient distress. If untreated, VT can lead to other dangerous life-threatening conditions, such as the development of blood clots, which can cause stroke and possibly death.

Treatment for tachycardia may include anti-tachycardia pacing (ATP) or cardioversion, in which a train of high rate pulses of one or more high energy pulses is delivered to the heart in an attempt to restore a more normal rhythm. ATP is typically effective in converting stable atrial tachycardias to normal rhythm, and is often delivered via an implanted device. In many cases, a sequence of increasingly aggressive ATP therapies are applied until the VT episode is terminated. The implanted device can be configured to discontinue ATP and immediately apply cardioversion in the event the VT degrades into VF.

SUMMARY

In general, the invention is directed to ATP techniques that make use of a history-dependent pacing interval determination for ATP pacing pulses. The ATP techniques described here are useful for delivering ATP pulses used to treat VT. In addition, the ATP techniques may be useful for treatment of atrial tachycardia (AT).

A patient may experience a tachycardia at any time, such as during rest when the heart beats at a normal rate, or during exercise when the heartbeat is accelerated from the normal rate. Therefore, an ATP therapy that is effective during periods of rest may not be as effective during active periods in which heart rates are accelerated.

The ATP therapy delivered in accordance with the invention is configured to take into account the heart rate prior to the detection of the tachycardia and during the course of the tachycardia episode in order to determine a more appropriate pacing interval for the ATP pacing pulses.

As will be explained, the ATP therapy takes into account differences in the action potential duration (APD) as a result of the prevailing heart rate prior to detection of the AT or VT. As higher heart rates persist, for example, the APD typically decreases. On the other hand, the APD typically increases in the presence of slower heart rates. Accordingly, the invention takes advantage of this phenomenon in determining the ATP pacing interval more appropriate for the circumstances.

In one embodiment, the invention provides a method that includes detecting a tachycardia within a heart, applying anti-tachycardia pacing pulses to the heart, and setting a pacing interval of the anti-tachycardia pacing pulses based on an estimate of action potential duration within the heart at the time of application of the anti-tachycardia pacing pulses.

In another embodiment, the invention provides a device that includes at least one electrode to detect electrical activity associated with a tachycardia, and a processor that determines an estimate of action potential duration and sets a pacing interval of anti-tachycardia pacing pulses based on the estimate of action potential duration within a heart at a time of application of the anti-tachycardia pacing pulses.

In yet another embodiment, the invention is directed to a computer-readable medium containing instructions for carrying out the techniques described above.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
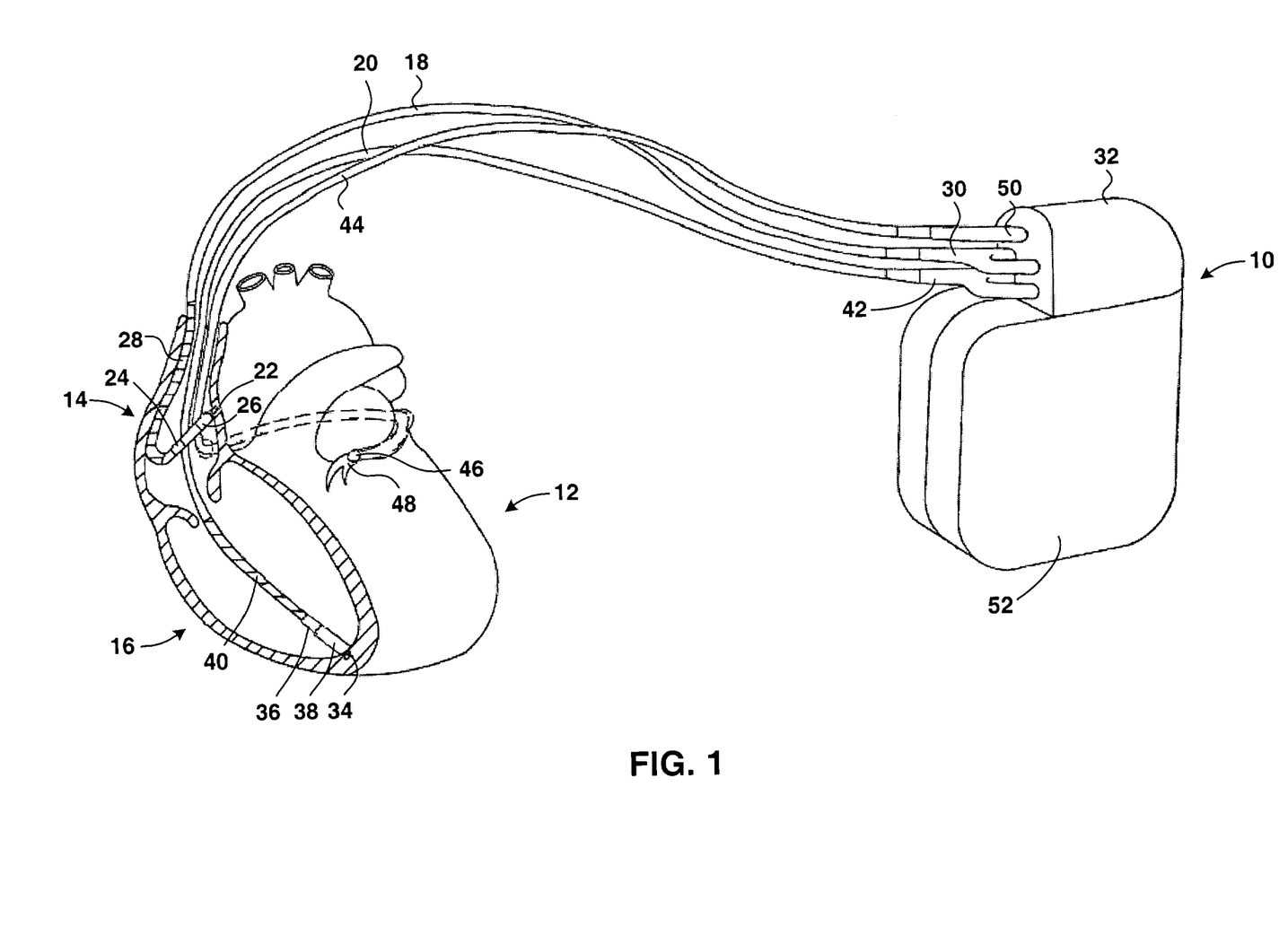
FIG. 1 is a schematic illustration of an implantable pacemaker/cardioverter/defibrillator with leads extending to a human heart.

FIG. 1 depicts an exemplary implantable medical device (IMD) 10 for implementing the techniques of the invention. IMD 10 delivers ATP techniques that make use of a history-dependent pacing interval determination for ATP pacing pulses. In this manner, IMD 10 provides a dynamic ATP pacing interval that is responsive to the heart rate prior to tachycardia detection and during the course of the tachycardia episode. This dynamic pacing interval determination takes into account the effect of the pacing interval in terminating tachycardia episodes that are preceded by different heart rates. More particularly, the ATP therapy delivered by IMD 10 takes into account differences in the action potential duration (APD) as a result of the prevailing heart rate prior to detection of the AT or VT. As a result, IMD 10 is able to dynamically deliver different pacing intervals that are more effective for a given tachycardia episode.

In the example of FIG. 1, IMD 10 is an implantable multi-chamber pacemaker that includes anti-tachycardia pacing (ATP), cardioversion and defibrillation capabilities.

The invention is not limited to the particular IMD and configuration shown in FIG. 1, however, but may be practiced by any number of implantable medical devices. The techniques of the invention may be practiced by a device that paces a single cardiac chamber or several chambers, that paces one or more atria or one or more ventricles, that includes or lacks cardioversion and defibrillation capability, and that paces in any of several pacing modes. In general, the techniques of the invention may be practiced by any device that supplies ATP therapy, whether to the atria to treat AT, or to the ventricles to treat VT.

As shown in FIG. 1, IMD 10 includes circuitry corresponding to an implantable pulse generator (IPG) enclosed within a housing 52 that generates pacing stimuli to administer one or more ATP therapies to heart 12. In some circumstances, the IPG generates pacing stimuli for purposes other than ATP, e.g., to perform antibradycardia pacing. In the embodiment shown in FIG. 1, pacing stimuli are applied to the right atrium 14 or the right ventricle 16, or both. IMD 10 also includes circuitry to sense atrial and ventricular activations, including activations generated during episodes of atrial tachycardia (AT) or ventricular tachycardia (VT). Atrial and ventricular bipolar pace/sense electrode pairs at the distal ends of leads 18 and 20, respectively, carry out the pacing and sensing functions.

In right atrium 14, the distal end of atrial lead 18 includes an extendable helical, pace/sense tip electrode 22 and a pace/sense ring electrode 24. Helical electrode 22 extends from electrode head 26 into the atrial appendage. Pace/sense electrodes 22 and 24 are employed for atrial pacing, including delivery of atrial ATP therapies, and for sensing of P-waves indicative of atrial activation. The distal end of atrial lead 18 also includes an elongated coil defibrillation electrode 28 that can deliver a defibrillation shock to right atrium 14. Electrode 28 may also be used to deliver cardioversion therapy to right atrium 14.

Cardioversion therapy typically involves delivery of less energy to heart 12 than defibrillation therapy, but both cardioversion and defibrillation therapies are painful to the patient. ATP therapies, by contrast, involve far less energy than cardioversion and defibrillation therapies. ATP therapies are often well-tolerated by patients, and in some cases, ATP therapies proceed without the patient becoming aware of the therapies. ATP and cardioversion may both be effective in terminating AT, but when ATP is as effective as cardioversion in terminating AT, ATP is favored over cardioversion to avoid causing the patient undue discomfort.

Atrial lead 18 includes conductors that electrically couple electrodes 22, 24 and 28 to IMD 10. The conductors are arranged in any desired configuration, such as coaxially, coradially, or in parallel, and are insulated from one another and from the tissue of the patient. In the example of FIG. 1, the proximal end of atrial lead 18 includes a bifurcated connector 30 that couples the conductors to a connector block 32 on IMD 10.

In right ventricle 16, the distal end of ventricular lead 20 likewise includes a pace/sense tip electrode 34 and a pace/sense ring electrode 36. Pace/sense tip electrode 34 may be a helical electrode that extends from electrode head 38 toward the apex of heart 12. Pace/sense electrodes 34 and 36 are employed for ventricular pacing, including delivery of ventricular ATP therapies, and for sensing of R-waves indicative of ventricular activation. The distal end of ventricular lead 20 also includes an elongated coil defibrillation electrode 40 that can deliver a defibrillation shock or cardioversion therapy to right ventricle 16. As noted above, cardioversion and defibrillation therapies are painful. Ventricular ATP therapies cause considerably less discomfort to the patient, and may be as effective in terminating a given episode of VT as cardioversion.

Like atrial lead 18, ventricular lead 20 includes one or more insulated conductors that electrically couple electrodes 34, 36 and 40 to IMD 10. As shown in FIG. 1, the proximal end of ventricular lead 20 includes a bifurcated connector 42 that couples the conductors to connector block 32.

FIG. 1 further illustrates deployment of a coronary sinus lead 44. Coronary sinus lead 44 includes one or more insulated conductors. The proximal end of coronary sinus lead 44 includes one or more electrodes, such as pace/sense electrode 46. Pace/sense electrode 46 is deployed within the great vein 48 of heart 12, and e used to deliver pacing therapies, including ATP therapies, to the left side of heart 12. A connector 50 at the proximal end of the coronary sinus lead 44 couples the conductors in lead 44 to connector block 32. In some embodiments of the invention, coronary sinus lead 44 includes an elongated exposed coil wire defibrillation electrode (not shown).

IMD 10 includes housing 52 that, in some embodiments of the invention, serves as a "can" electrode. In unipolar operation, IMD 10 delivers an electrical stimulation to heart 12 via an electrode disposed on one or more of leads 18, 20 or 44, with housing 52 being a part of the return current path. In bipolar operation, by contrast, IMD 10 delivers an electrical stimulation to heart 12 via a tip electrode, with a ring electrode providing the principal return current path.

In the embodiment depicted in FIG. 1, IMD 10 delivers pacing stimuli to right atrium 14 and right ventricle 16 via electrodes 22 and 34, respectively, and senses activations via the same electrodes. The electrodes sense the electrical activity that accompanies AT or VT. The electrodes also deliver one or more ATP therapies to treat AT, VT, or both.

IMD 10 may be programmed to administer more than one ATP therapy. ATP therapies may differ from one another by the manner in which pacing pulses are applied to heart 12 to terminate AT or VT. One ATP therapy, for example, delivers a sequence of pacing pulses separated from one another by constant pacing intervals, while another ATP therapy delivers a sequence of pacing pulses separated from one another by pacing intervals that shorten with each pulse in the series. In either case, the pacing interval for each sequence is history-dependent in the sense that it is determined as a function of the heart rate, i.e., cycle length, prior to detection of the pertinent tachycardia. The number of pulses in the ATP therapies may vary from one therapy to another. IMD 10 may also be programmed to administer cardioversion therapy at more than one energy level, and programmed to deliver cardioversion therapies according to a hierarchy.

The invention provides techniques for estimating the action potential duration (APD) of heart 12 in order to more accurately set a pacing interval for ATP pulses. As will be described in greater detail below, the estimate of APD is obtained as a function of one or more heart electrical characteristics over a period of time. The heart electrical characteristics comprise P-waves, R-waves and T-waves that IMD 10 detects via electrodes 22, 24, 34 and 36. In some embodiments, IMD 10 includes a T-wave detection module (not shown) to more accurately detect T-waves and hence the APD. Furthermore, IMD 10 can detect the cycle length of a tachycardia using heart electrical characteristics, which further aids in setting the pacing interval for ATP pulses accurately. The invention may also provide a technique for setting pacing intervals for subsequent ATP sequences based on further estimates of APD and cycle lengths of detected tachycardia should a prior ATP therapy using a first pacing interval fail to terminate the pertinent tachycardia.

The goal of an ATP therapy is to terminate a detected tachycardia, which allows the heart to resume a normal rhythm. A proper time interval in which to terminate the detected tachycardia is shortly after the APD but before the tachycardia pulse. The ATP fails to terminate the tachycardia when an ATP pulse occurs at a time outside of the proper time interval. For example, an ATP therapy applied during the APD will fail as well as an ATP therapy applied near a tachycardia pulse. In fact, an ATP therapy applied too near a tachycardia pulse, may have an opposite desired effect, in that the ATP therapy may accelerate the tachycardia into fibrillation. The estimate of APD is used to determine a starting point of the proper time interval and the cycle length of a detected tachycardia is used to determine an end point of the proper time interval. IMD 10 uses the estimate of APD and the cycle length of a detected tachycardia to define the proper time interval, thus enabling IMD 10 to set a pacing interval such that ATP pulses are applied during the proper time interval. Setting the pacing interval of the ATP pulses to coincide with this interval of time increases the ability of IMD 10 to terminate the detected tachycardia, reducing the likelihood that the tachycardia will degrade into fibrillation, reducing the number of pulses delivered to heart 12 and increasing the battery life of IMD 10.

The APD has been observed to vary as a function of the prevailing heart rate prior to detection of the tachycardia and during the tachycardia episode. As higher heart rates persist, for example, the APD typically decreases. On the other hand, the APD typically increases in the presence of slower heart rates. Accordingly, the invention takes advantage of knowledge of the correlation between recent heart rate history and APD to determine an ATP pacing interval that is more likely to be effective under certain circumstances. More effective ATP therapies will decrease the probability of VT or AT accelerating to VF or AF, respectively, which is beneficial in that such fibrillation events are more dangerous. Techniques to estimate the APD and determine the pacing interval of ATP pulses based on the estimate of APD and a cycle length of a detected tachycardia will be described in more detail below.

Figure 2:
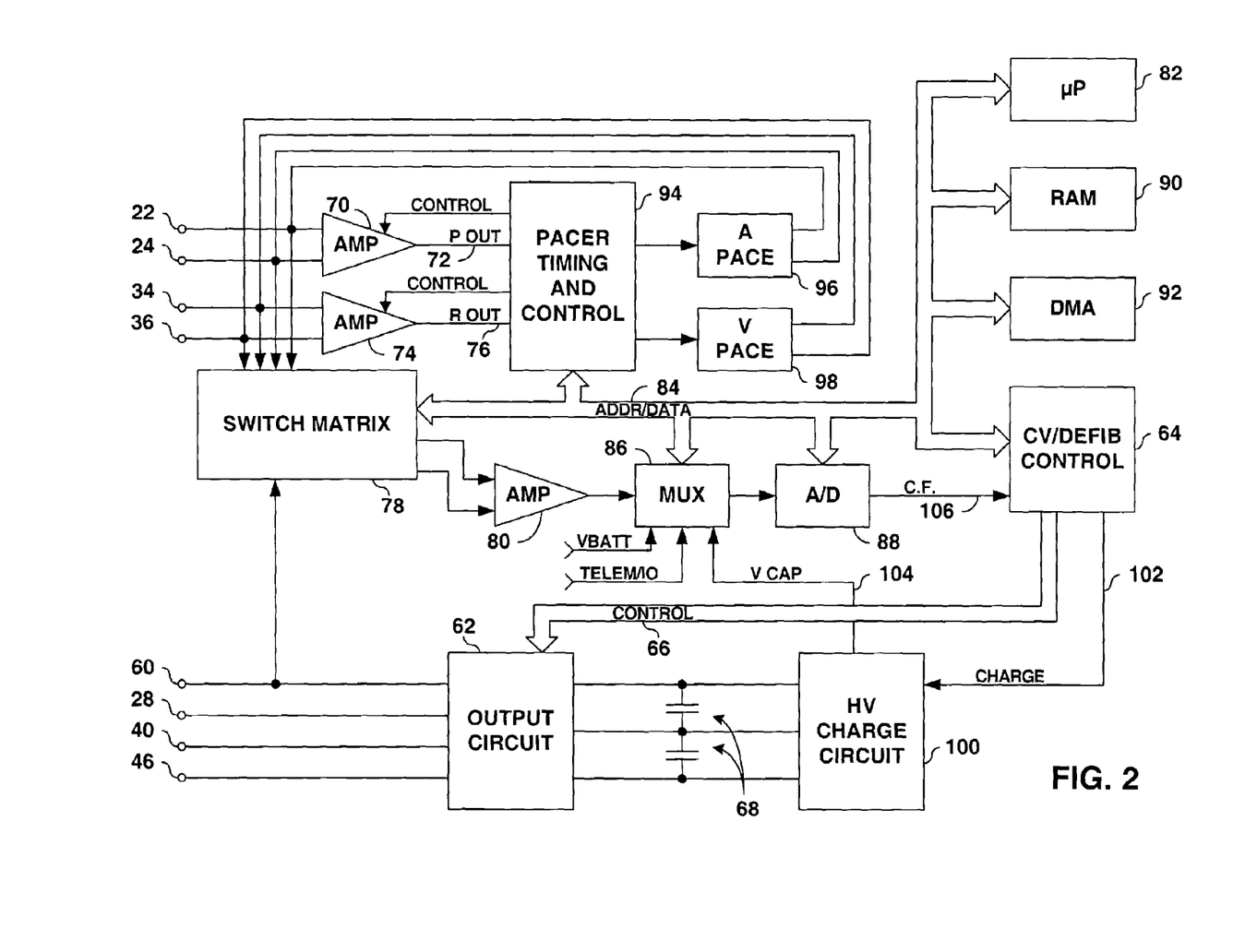
FIG. 2 is a block diagram of the components of the implantable medical device depicted in FIG. 1.

FIG. 2 is a functional schematic diagram of one embodiment of IMD 10 and illustrates how IMD 10 detects episodes of tachycardia and delivers therapies, such as ATP and cardioversion, to address the episodes. IMD 10 of FIG. 2 is exemplary of the type of device in which various embodiments of the invention may be embodied, and the invention is not limited to the particular schematic shown. On the contrary, the invention may be practiced in a wide variety of devices, including single- and multi-chamber devices, and implantable devices that do not include cardioversion or defibrillation pacing capability.

As shown in FIG. 2, IMD 10 includes electrode terminals 22, 24, 28, 34, 36, 40 and 46, which correspond to the electrodes shown in FIG. 1. Electrode 60 corresponds to the un-insulated portion of housing 52 of IMD 10. Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation or cardioversion shocks.

Electrodes 22 and 24, located on or in right atrium 14, are coupled to a P-wave amplifier 70. Amplifier 70 includes an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold. The time intervals between signals on P-out line 72 reflect the cycle length of atrial activations, and may be indicative of whether the patient is experiencing an episode of AT. In particular, short cycle lengths may be indicative of AT.

Electrodes 34 and 36, located in right ventricle 16, are coupled to an R-wave amplifier 74. Amplifier 74 includes an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74. The time intervals between signals on R-out line 76 reflect the cycle length of ventricular activations and may be indicative of whether the patient is experiencing an episode of VT.

As noted above, cycle length may be one of the tachycardia characteristics associated with a therapy or a hierarchy of therapies. In some patients, it may be possible to distinguish one type of tachycardia from another by cycle length. In these patients, IMD 10 may be able to implement a power-saving mode. IMD 10 is powered by a self-contained power source such as a battery (not shown in FIGS. 1 and 2). Determining a tachycardia characteristic by determining an ATP pacing interval as a function of tachycardia cycle length generally consumes less power than determining other tachycardia characteristics, such as morphology. Consequently, the capability of distinguishing one tachycardia from another by cycle length may preserve the battery life of IMD 10.

A switch matrix 78 selects electrodes for coupling to a wide band amplifier 80 for use in digital signal analysis. Selection of electrodes is controlled by microprocessor 82 via data/address bus 84. The signals from the selected electrodes are provided to multiplexer 86, and are thereafter converted to multi-bit digital signals by A/D converter 88. The signals are stored in random access memory (RAM) 90 under control of direct memory access (DMA) circuit 92.

Digital signal analysis includes, but is not limited to, a morphological analysis of waveforms sensed by the selected electrodes. Morphological analysis includes wavelet analysis, Fourier analysis or similar spectral analysis techniques, but the invention is not limited to those analytical techniques. Microprocessor 82 employs digital signal analysis techniques to characterize the digitized signals stored in RAM 90 to recognize and classify the patient's heart rhythm or to determine the morphology of the signals employing any of several signal processing methodologies. In particular, microprocessor 82 may use morphological analysis to determine the occurrence of T-waves.

A T-wave detection module (not shown) may be included, and formed by various components cooperating to detect the occurrence of T-waves. The various components forming the T-wave detection module may include, for example, microprocessor 82, RAM 90, A/D converter 88 and DMA circuit 92. These components cooperate to detect the T-wave signal, which provides an accurate estimate of the APD.

Signals sensed via electrodes 22, 24, 34 and 36 may be used to determine whether to administer cardiac pacing, ATP, cardioversion or defibrillation therapies. Pacer timing/control circuitry 94 receives signals from P-out line 72 and R-out line 76, and computes various timing intervals as a function of the timing of the received signals. Pacer timing/ control circuitry 94 also may include programmable digital counters that control pacing according to any of several pacing modes.

Pacer output circuitry 96 and 98, which are coupled to electrodes 22, 24, 34 and 36, generate pacing and ATP stimuli under the control of pacer timing/control circuitry 94. The IPG of IMD 10 includes microprocessor 82, in cooperation with pacer timing/control circuitry 94 and pacer output circuitry 96 and 98.

Pacer timing/control circuitry 94 also computes intervals such as R-R intervals, P-P intervals, P-R intervals and R-P intervals. These intervals are used to detect the presence of a fast heart rate, which may be an indicator of a tachycardia. A fast heart rate may also be indicative of sinus tachycardia, i.e., a fast heart rate in response to a physiological stimulus, such as exercise.

Microprocessor 82 and pacer timing/control circuitry 94 cooperate to apply any of a number of algorithms to discriminate a tachycardia such as VT or AT, for which anti-tachycardia therapy is indicated, from sinus tachycardia, for which therapy is not indicated. Microprocessor 82 and pacer timing/control circuitry 94 further cooperates to apply any of a number of algorithms to discriminate a tachycardia such as VT or AT, which terminates in response to antitachycardia therapies, from other tachyarrhythmias such as atrial fibrillation and ventricular fibrillation, which generally do not respond to antitachycardia therapies. The invention may be practiced with any algorithm or algorithms that detect an atrial or ventricular tachycardia.

When IMD 10 detects an atrial or ventricular tachycardia, microprocessor 82 determines the tachycardia cycle length and configures an ATP therapy by setting the pacing interval of the ATP pulses based on an estimate of the action potential duration (APD) and the tachycardia cycle length, in accordance with the invention. The before mentioned R-R intervals, P-P intervals or T-wave signals serve as a basis for the APD estimate. In some embodiments, microprocessor 82 may continually calculate the estimate of APD over a window of time, which slides forward as time progresses. The calculation is stored in RAM 90 for use in further calculations of the estimate of APD. RAM 90 also stores a heart rate, a diastolic interval and the like. If the first ATP therapy fails to terminate the tachycardia, a second ATP therapy is applied and so on. Consecutive therapies may apply pacing intervals based on further, more current APD estimates that have been gathered within the sliding window of time. In this manner, IMD 10 updates the ATP pacing interval in subsequent ATP pacing sequences based on updated APD estimates. Other parameters pertaining to the ATP therapy may change such as the tachycardia cycle length regularity or tachycardia waveform morphology.

For each ATP therapy that is applied, microprocessor 82 loads parameters such as pacing interval from RAM 90 into pacer timing/control circuitry 94, which controls delivery of the ATP therapy. Microprocessor 82 evaluates the outcome of the ATP therapy, and determines whether ATP therapy should be discontinued or whether another therapy ought to be applied.

In some circumstances, a tachycardia may be unresponsive to all ATP therapies. In some of those circumstances, cardioversion may be indicated. Cardioversion therapies, like ATP therapies, may differ from one another and may be arranged in a hierarchy, with the first cardioversion therapy in the hierarchy applied first, the second cardioversion therapy in the hierarchy applied if the first fails, and so on.

When a cardioversion or defibrillation pulse is required, microprocessor 82 controls the timing, strength and duration of cardioversion and defibrillation pulses. In response to the detection of atrial or ventricular fibrillation or tachycardia requiring a cardioversion pulse, microprocessor 82 activates CV/defib control circuitry 64, which initiates charging of capacitor bank 68 via charging circuit 100, under the control of high voltage charging control line 102. The voltage on the high voltage capacitors is monitored via VCAP line 104, which is passed through multiplexer 86, and in response to reaching a predetermined value set by microprocessor 82, results in generation of a logic signal on Cap Full (CF) line 106 to terminate charging. Output circuit 62 then delivers a defibrillation or cardioversion pulse.

Figure 3:
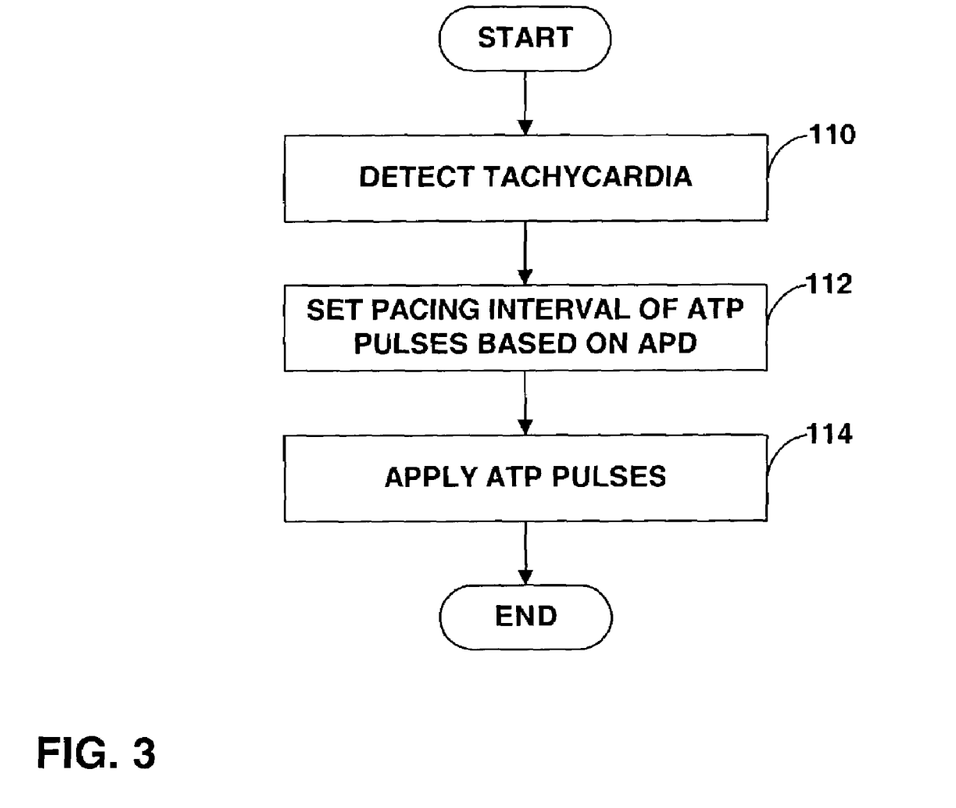
FIG. 3 is a flow diagram illustrating an exemplary method for applying an ATP therapy with a history-dependent pacing interval determination.

FIG. 3 is a flow diagram illustrating an exemplary process for applying an ATP therapy whereby a pacing interval of the anti-tachycardia pacing (ATP) pulses is a function of an estimate of action potential duration (APD) of a heart and a cycle length of a tachycardia within the heart. The process begins when a device, such as IMD 10 of FIG. 1, detects a tachycardia (110) within heart 12, e.g., based on a heightened heart rate. The tachycardia occurs in either the atrium or the ventricle, and IMD 10 may detect tachycardia occurring in both via electrodes, such as electrodes 22, 24, 34, and 36.

Upon detecting the tachycardia, microprocessor 82 (FIG. 2) determines the cycle length of the detected tachycardia. Microprocessor 82, then accesses a memory address within RAM 90 where an estimate of the APD is stored. Microprocessor 82 calculates the pacing interval of an ATP therapy as a function of the APD and cycle length of the detected tachycardia. Microprocessor 82 further loads the pacing interval into pacer timing and control circuit 94. The act of loading the pacing interval into pacer timing and control circuit 94 sets the pacing interval of the ATP pulses (112) to be delivered to heart 12.

IMD 10 applies the ATP pulses for the current ATP sequence (114) to heart 12. The pulses are timed to have a pacing interval that reflects the pacing interval determined as a function of the estimate of APD of heart 12. Setting the pacing interval based on the estimate of APD is described below in more detail.

Figure 4:
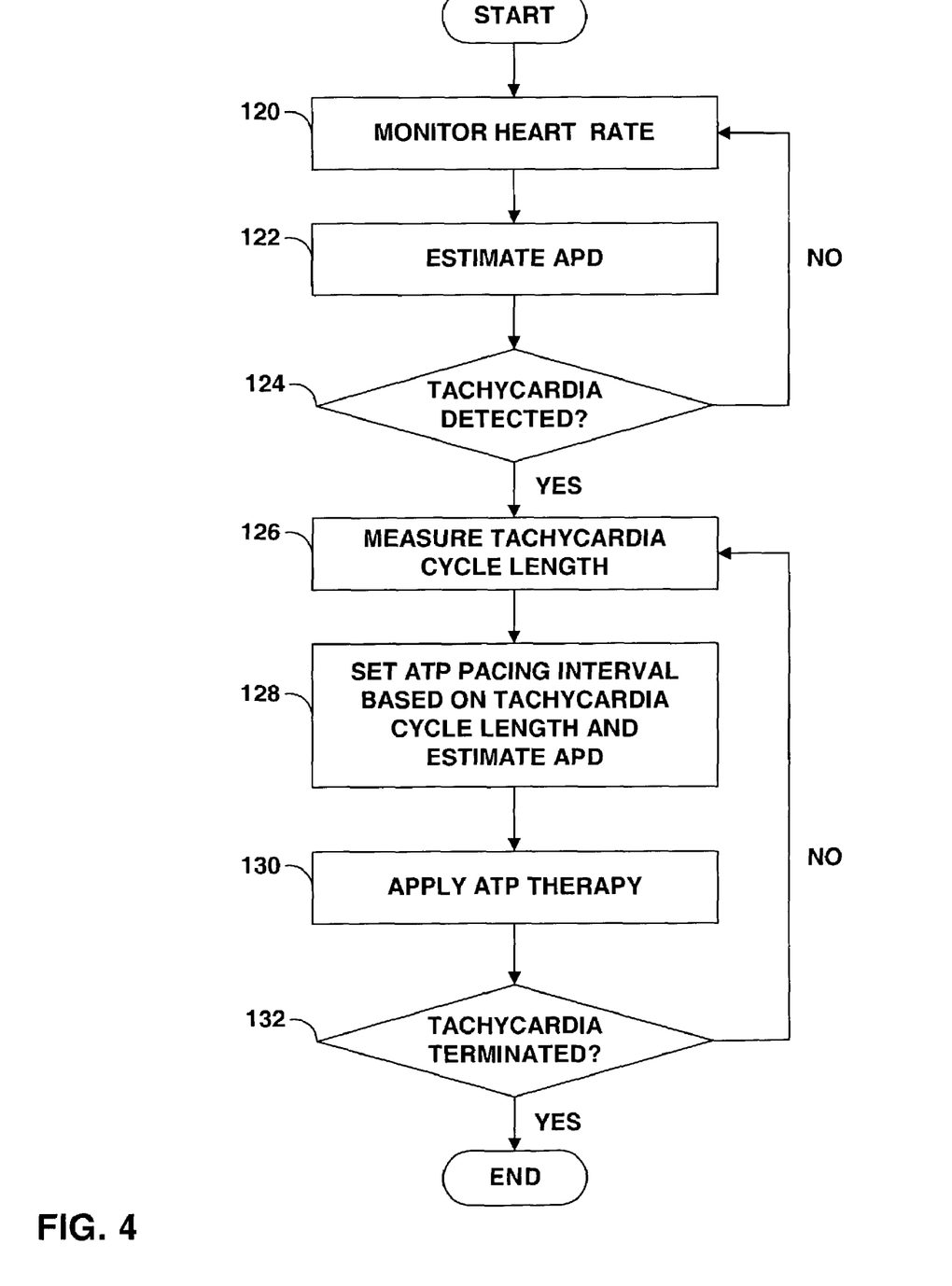
FIG. 4 is a flow diagram illustrating the method of FIG. 3 in greater detail.

FIG. 4 is a flow diagram illustrating the process of FIG. 3 in greater detail. In particular, FIG. 4 further depicts determination of the pacing interval of ATP pulses such that the pacing interval is a function of an estimate of APD of a heart and cycle length of a detected tachycardia within the heart. For an ATP therapy to be effective, an ATP pulse should occur within a particular interval of time relative to the APD and cycle length of a tachycardia. The pacing interval determines when the ATP pulses occur and whether the pulses occur during the particular interval of time.

The process of setting the pacing interval begins with IMD 10 monitoring the heart rate (120) of a heart 12. IMD 10 may determine the heart rate in a variety of ways. In general, the heart rate can be determined using heart electrical characteristics, such as P-wave signal or R-wave signals and their respective intervals, such as P-P, R-R intervals, and the like. IMD 10 may determine these intervals as described above. Microprocessor 82 (FIG. 2) may use one of the intervals to calculate an estimate of the APD (122) of heart 12. The APD is one factor that aids in setting the pacing interval.

The pacing interval is set in response to the characteristics of a tachycardia. If a tachycardia is not detected (124), then IMD 10 continues to monitor the heart rate and estimate the APD over a period of time. IMD 10 estimates the APD over a period of time, which slides forward as time progresses. Microprocessor 82 stores the estimate of the APD to RAM 90 when the estimated APD changes or when the estimate of APD is calculated. IMD 10 continually estimates APD over a sliding window of time and stores the estimate of APD until IMD 10 detects a tachycardia.

When IMD 10 detects a tachycardia, pacer timing and control circuit 94 measures the cycle length of the tachycardia. The cycle length of the tachycardia is another factor that aids in setting the pacing interval of the ATP pulses. IMD 10 may determine the cycle length of the tachycardia in the manner described above (126), e.g., by reference to the P-P interval or the R-R interval.

Generally, an ATP pulse is most effective when applied shortly after the end of the APD but before the next tachycardia pulse. This period of time is when an ATP pulse is most likely to terminate the detected tachycardia within the heart. Terminating the tachycardia is essential to return of the heart to a normal rhythm. Thus, IMD 10 sets the pacing interval of the ATP pulses, such that the ATP pulses occur during this period of time, shortly after the APD ends but before the next tachycardia pulse. IMD 10 uses the estimate of APD to determine when the APD is likely to end. IMD 10 further uses the cycle length of the tachycardia to determine when the next tachycardia pulse is likely to occur. These two parameters are used to set the ATP pacing interval (128) such that an ATP pulse will occur shortly after the APD but before the tachycardia pulse.

After the pacing interval of the ATP therapy is set, IMD 10 applies the ATP therapy (130). The therapy may be a sequence including any number of ATP pacing pulses applied in a variety of forms, but with the pacing interval determined in view of the estimated APD. For example, the rate of the pulses may ramp such that the rate of the pulses increases from start to finish. Also, IMD 10 may deliver triangular pulses, square pulses or any other pulse morphology consistent with the invention.

Heart 12 may not immediately respond to the ATP therapy, as described above. The tachycardia may not terminate after the ATP therapy is applied (132). When the tachycardia does not terminate, IMD 10 calculates another estimate of the APD of heart 12 and can further determine the cycle length of the detected tachycardia to ensure the cycle length has not changed. The new estimate is used in conjunction with the newly determined tachycardia cycle length to determine another pacing interval for the next ATP therapy sequence.

The new pacing interval is set and the ATP therapy is applied. Again, IMD 10 determines if the therapy terminated the detected tachycardia. The tachycardia may persist and the process may repeat until the tachycardia is terminated, or IMD 10 determines that another therapy, such as cardioversion, is needed. Once the tachycardia terminates, IMD 10 returns to monitoring the heart rate and estimating the APD. The process used to estimate the APD is described in detail below.

Figure 5:
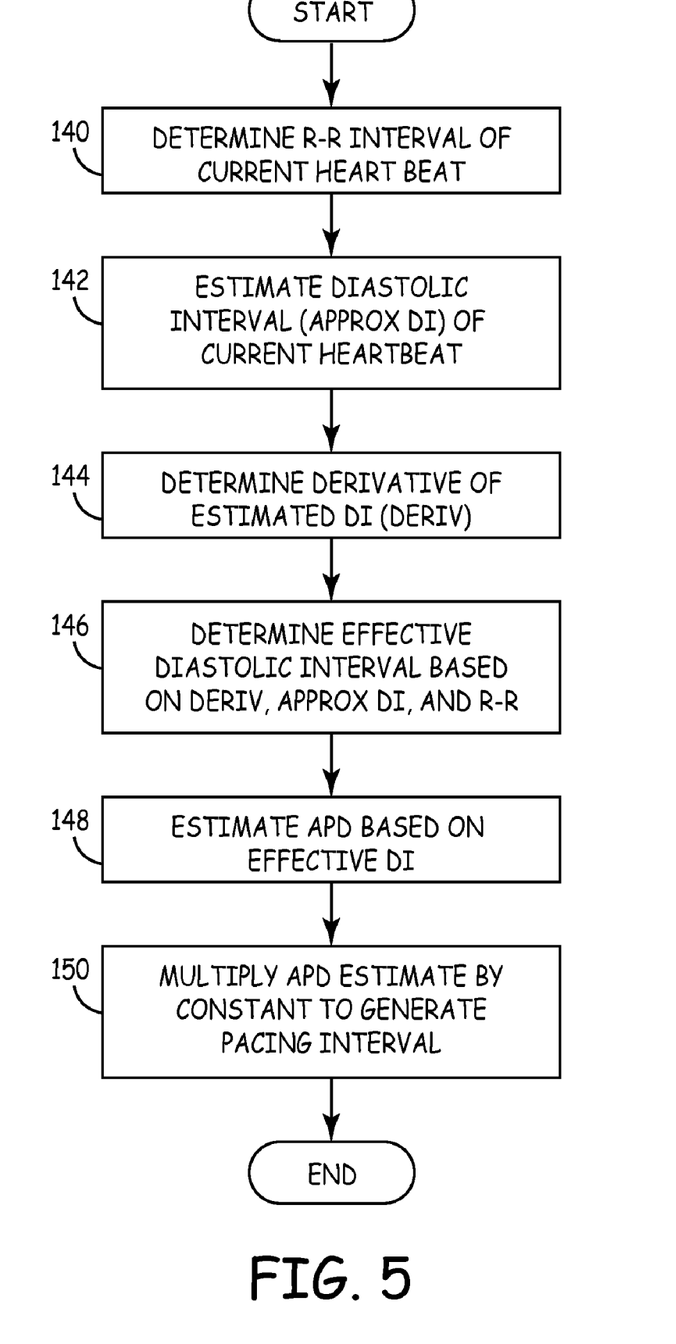
FIG. 5 is a flow diagram illustrating an exemplary method for estimating an APD within a heart.

FIG. 5 is a flow chart illustrating an exemplary process for calculating an estimate for an APD of a heart. The heart proceeds through two phases: the systolic phase and the diastolic phase. APD is a term used when referring to a time interval of the systolic phase while a diastolic interval refers to a time interval of the diastolic phase. Thus the APD and diastolic interval relate to each other and when added together form the cycle length of a single heartbeat. Microprocessor 82 of FIG. 2 may use this relationship and other relationships consistent with the principles of the invention to determine an estimate for the APD of the heart, such as heart 12 (FIG. 1).

The APD is further estimated over a period of time. In one embodiment of the invention the period of time is a sliding window, which slides forward as time progresses. As the sliding window progresses forward, microprocessor 82 continually estimates the APD and resets the pacing interval as the APD estimate changes. Since efficiency is important for implantable devices, such as IMD 10, the estimate of APD is done in a discrete manner by sampling signals using A/D converter 88. The signals sampled may include R-wave signals, P-wave signals or T-wave signals as detected by a T-wave detection module. Electrodes in the atrium, such as electrodes 22 and 24, and electrodes in the ventricle, such as electrodes 34 and 36, detect these signals by the process described above. Pacer timing and control circuit 94 determines R-R intervals, P-P intervals and T-T intervals, which reflect an interval of a single heartbeat (140).

An approximation of the current diastolic interval is not needed if IMD 10 includes a T-wave detection module. The diastolic interval is defined by the interval of time between the end of a T-wave signal and the beginning of an R-wave signal. Accordingly, with the T-wave detection module, IMD 10 can directly determine the diastolic interval. Without the T-wave detection module, however, IMD 10 estimates the diastolic interval of the current heartbeat (142). Microprocessor 82 extrapolates past diastolic intervals to approximate the diastolic interval of the current heartbeat. The extrapolation involves both past APDs and past diastolic intervals to increase the accuracy of the approximation.

The interval of the current heartbeat, as determined by the P-P or R-R interval, is used when determining a time constant, or response over time to change within a system. In the case indicated here, where the estimate of the APD is generated, the time constant refers to the response over time to the change of the diastolic interval ($\Delta_n$) plus the cycle length of the current heartbeat ($T_n$). The time constant ($\alpha_n$) can be calculated according to the following relationship:

$$\alpha_n = \gamma_1 * \Delta_n + \gamma_2 * T_n \tag{1}$$

$$\Delta_n = |di_n - di_{n-1}|/di_{n-1} \tag{2}$$

Equation (2) represents the change of the diastolic interval between the last diastolic interval ($di_{n-1}$) and the current diastolic interval ($di_n$). This is also a method to discretely quantify the derivative. There are two constants associated with equation (1), one of which, $\gamma_1$, is multiplied with the result of equation (2), while the second, $\gamma_2$, is multiplied with $T_n$. These constants determine how much change is propagated throughout the system. If $\gamma_1$ is large in relation to $\gamma_2$ then change between the diastolic intervals is accentuated. If $\gamma_2$ is large in relation to $\gamma_2$ then change is moderate while the current heartbeat interval is accentuated.

Microprocessor 82 uses equation (2) to estimate the derivative of the approximate diastolic interval (144). The result of equation (2) is used as input by microprocessor 82 into equation (1). The result of equation (1) is then used as input into the following equation, equation (3), where the effective diastolic interval ($di^e_n$) is determined.

$$di^e_n = di^e_{n-1} * (1 - \alpha_n) + \alpha_{n-1} * di_n \tag{3}$$

Equation (3) is an integral term that effectively accumulates all past approximate diastolic intervals within a given time period. Microprocessor 82 calculates the effective diastolic interval and updates a state variable within RAM 90 after each calculation. Equation (3) makes use of equation (1) and in effect determines how much of the estimated APD is determined by previous approximation of the diastolic interval and how much is determined by the current diastolic interval. In this example, the effective diastolic interval is based on the derivative of the approximate diastolic interval ($\Delta_n$), the approximate diastolic interval ($di_n$ and $di_{n-1}$) and the R-R interval for the current heartbeat ($T_n$) (146).

The result of equation (3) is used to determine an estimate of the APD (148). Microprocessor 82 calculates the results of each of the three prior equations. Microprocessor 82 may further access RAM 90 for any data needed, such as a past diastolic interval $di_{n-1}$, that is not readily available. Equation (4) as follows, determines the estimate of APD as a function of the effective diastolic interval, $di^e_n$.

$$APD(di^e_n) = APD_{max} - \sigma(DI_{max} - di^e_n) \quad (4)$$

Equation (4) above represents a piece-wise linear system having a constant value $APD_{max}$ after the diastolic interval $di^e_n$ reaches $DI_{max}$. Before $di^e_n$ reaches $DI_{max}$ the APD has a value of $APD_{max}$ subtracted by a relation with a constant slope ($\sigma$) times $DI_{max}$ minus $di^e_n$. $DI_{max}$ is a constant representing the maximum diastolic interval. The constants of equations (1) through (4) can modify the result yielding a more accurate estimate of APD.

Constants $\gamma_1$, $\gamma_2$, $\sigma$, $APD_{max}$ and $DI_{max}$ can be adjusted to tune the result of equation (4). For instance, $\gamma_1$ and $\gamma_2$ determine the amount of change that is propagated into the system used to estimate APD. The slope factor, $\sigma$, can modify the initial response of the system to fit expected data. $APD_{max}$ and $DI_{max}$ change the upper limits of the system allowing for a larger APD and diastolic interval (DI). Furthermore, the constants above allow for patient dependent configuration and can determine specific therapies that work best in the case of the patient.

An accurate estimate of the APD is desired so that IMD 10 can deliver a more effective ATP therapy. The above relations, equations (1)–(4), define a system for estimating the APD by continually evaluating electrical heart characteristic trends. For example, the electrical heart characteristics, such as the R-R interval, may decrease due to natural causes such as exercise. This is known as sinus tachycardia, which is a fast heart rate in response to a physiological stimulus. An estimate of the APD during sinus tachycardia may reflect the change in R-R interval. The rate at which the estimate of APD changes is dependent on the time constant ($\alpha_n$), which effects how quickly the system responds to the sinus tachycardia. A large time constant will cause the system to respond quickly while a small time constant will cause the system to respond slowly.

Figure 6:
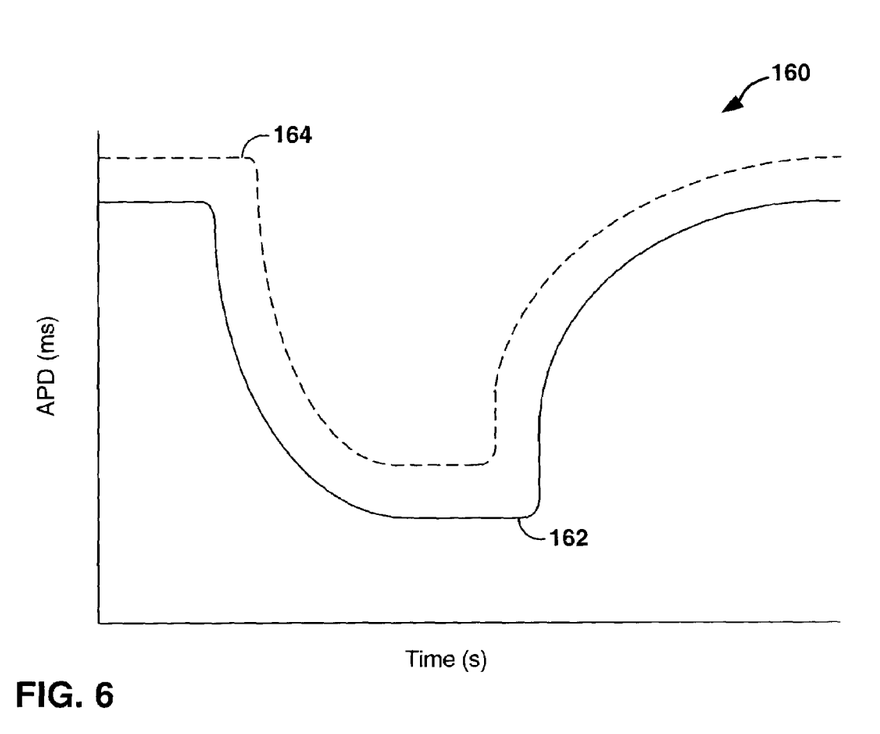
FIG. 6 is a graph illustrating changes in APD over time.

While the above patient is exercising a tachycardia may occur. In this case, IMD 10 would set the pacing interval dependent on the estimate of APD, which reflects the sinus tachycardia. Without the estimate of APD, most devices measure the cycle length of the tachycardia and multiply this value by a constant to set the pacing interval of the ATP pulses. Without an estimate of the APD, other approaches to setting the pacing interval do not reflect the current heart condition and can miss the interval of time where an ATP pulse may most effectively terminate the tachycardia. Devices, which embody the principles of the invention, more accurately determine the interval of time where an ATP pulse may terminate the tachycardia. FIG. 6 further illustrates estimating APD for accurate application of ATP pulses to more effectively terminate the detected tachycardia.

FIG. 6 is a graph illustrating two lines: a solid line representing an estimate of the APD over time and a dashed line representing where a device that embodies principals of the invention may apply ATP pulses. The y-axis of graph 160 represents the estimate of APD as measured in milliseconds and the x-axis of the graph 160 represents time as measured in seconds. Graph 160 contains solid line 162 and dashed line 164, which illustrate response to changes within a system to measure an estimate APD. The system includes a heart, the heart electrical characteristics and a device, such as IMD 10 of FIG. 1.

IMD 10 monitors the heart electrical characteristics using the monitored P-waves and R-waves to estimate the APD of the heart. One embodiment, described above in FIG. 5, demonstrated how IMD 10 estimates the APD of heart 12. The estimate of the APD is shown in graph 160 as solid line 162. The downward trend of solid line 162 shows a response whereby the estimate of APD shortened in response to a quickened heart rate, which might occur during exercise. The upward trend of solid line 162 further shows that the heart rate decreased, which may indicate an end to the exercise. Setting the constants of equations (1)–(4) may modify various aspects of line 162. For example, by increasing $\gamma_1$ of equation (1) the estimate of APD may respond to change more quickly. Thus, the slope of both the upward and downward trends may increase in magnitude becoming steeper. This change to $\gamma_1$ would cause the system to be more aggressive when treating a tachycardia.

Dashed line 164 is the result of multiplying the estimate of APD, solid line 162, by a constant (150 of FIG. 5). Microprocessor 82 (FIG. 2) may specify the constant as any number greater than one. If the constant was less than one then the ATP pulse would come before the end of the APD and the therapy would fail. Thus, microprocessor 82 should preferably specify the constant greater than one. The constant also may increase the aggressiveness of the system. If the constant is close to one then IMD 10 will apply pacing pulses near the end of the APD. If the constant is large then IMD 10 will apply pacing pulses well after the end of the APD pulse. The techniques of the invention further specify that the ATP pulse should occur before the tachycardia pulse. Thus, microprocessor 82 should not set the constant such that the ATP pulse comes after the tachycardia pulse. This interval of time, shortly after the APD but before the tachycardia pulse, is desired for capturing the heart. Techniques of the invention estimate the APD and measure the tachycardia cycle length to determine and set the pacing interval of the ATP pulses such that ATP pulses occur during this interval of time.

Figure 7:
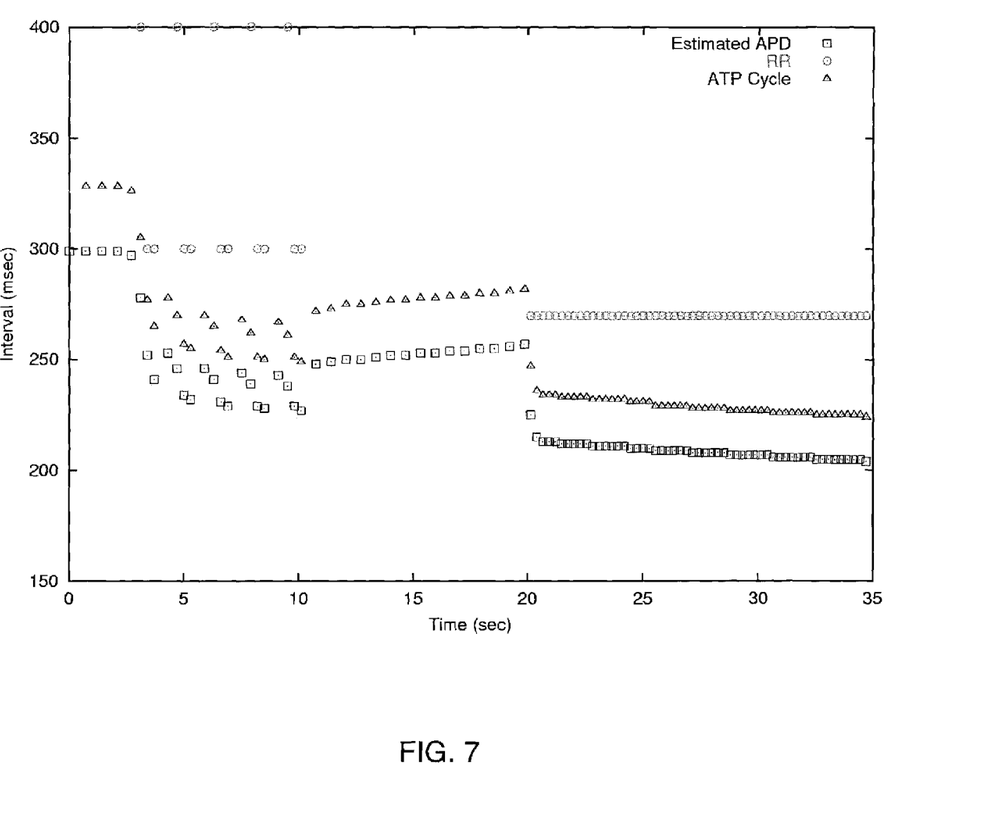
FIG. 7 is an exemplary graphical representation of a calculated R-R interval and a resulting estimated action potential duration (APD) generated by a number of RR-intervals occurring up to a point in time associated with the estimation of the APD.

FIG. 7 is an exemplary graphical representation of a calculated R-R interval and a resulting estimated APD generated by a number of RR-intervals occurring up to a point in time associated with the estimation of the APD. As illustrated in FIG. 7, the ATP cycle length is set so that ATP pulses, indicated by triangles, is set to remain between the estimated APD, indicated by squares, and the RR-intervals, indicated by circles, so that the ATP pulses follow the estimated APD at a predetermined distance from the estimated APD and less than the RR-interval, as described above. Note that at the end of the graphical representation, although the RR-interval remains constant, the ATP pulses follow the estimated APD and therefore decrease, rather than remaining constant as would be the case if the pacing pulses were merely set as a percentage of the RR-intervals.

Estimating an APD of a heart may allow for more accurate ATP pulse delivery to the heart. The more accurate delivery is defined by more accurate delivery of an ATP pulse during an interval of time where the pulse may more readily capture the heart. This interval of time begins shortly after the APD pulse and ends when the detected tachycardia pulse occurs.

By estimating the APD, a more accurate interval of time is determined in which ATP pulses may occur to capture the heart.

In addition, estimating the APD also allows a device consistent with the principles of the invention to base the pacing interval of ATP pulses on the current heart rate. Thus, if the heart rate increases, the estimate of APD decreases and the pacing interval of ATP pulses also decreases reflecting the change in heart rate. Generally, this will increase the outcome of an applied ATP therapy in situations where the heart is not beating at normal resting rates, such as exercise.

The invention further provides for the application of less ATP therapies due to the more accurate delivery of ATP pulses, which creates less power consumption and a longer battery life of a device utilizing the techniques of the invention. Battery life is an important factor when considering implantable devices since replacing a battery requires a surgical procedure. More accurate delivery of ATP pulses also results in more accurate ATP therapies, which decreases the probability of a tachycardia accelerating to a more dangerous fibrillation. Furthermore, the more accurate ATP therapy can help prevent the application of long, unsuccessful ATP therapies, which may allow the patient to lose consciousness before the therapy is effective.

Some of the techniques described above may be embodied as a computer-readable medium comprising instructions for a programmable processor such as microprocessor 82 or pacer timing/control circuitry 94 shown in FIG. 2. The programmable processor may include one or more individual processors, which may act independently or in concert. A "computer-readable medium" includes but is not limited to read-only memory, Flash memory and a magnetic or optical storage medium. The medium includes instructions for causing a processor to detect a tachycardia within a heart, estimate an APD based on a heart rate over a period of time prior to the detection of the tachycardia and set a pacing interval of the ATP pulses based on the estimate of APD. The medium may also include instructions for causing a programmable processor to estimate the APD using the interval between P-waves signals, the interval between R-wave signals and T-wave signals. The medium may further include instructions for causing a programmable processor to estimate a second APD, whereby the pacing interval of the ATP pulses is based on the second estimate of APD.

These and other embodiments are within the scope of the following claims.

The invention claimed is:

1. A method, comprising:
   detecting a tachycardia within a heart;
   estimating an action potential duration based on a heart rate over a period of time prior to the detection of the tachycardia;
   applying anti-tachycardia pacing pulses to the heart; and
   setting a pacing interval of the anti-tachycardia pacing pulses based on the estimate of action potential duration within the heart during application of anti-tachycardia pacing pulses.

2. A method comprising:
   detecting a tachycardia within a heart;
   applying anti-tachycardia pacing pulses to the heart; and
   setting a pacing interval of the anti-tachycardia pacing pulses based on an estimate of action potential duration within the heart during application of the anti-tachycardia pacing pulses, wherein setting a pacing interval of the anti-tachycardia pacing pulses based on an estimate of action potential duration includes estimating the action potential duration based on heart rate over a period of time prior to the detection of the tachycardia.

3. The method of claim 2, wherein the period of time is a sliding window that moves forward as time progresses, the method further comprising resetting the pacing interval as time progresses based on the heart rate within the sliding window.

4. The method of claim 1, wherein setting a pacing interval of the anti-tachycardia pacing pulses based on an estimate of action potential duration includes setting the pacing interval of the anti-tachycardia pacing pulses such that the pacing interval of the anti-tachycardia pacing decreases as the estimation of the action potential duration decreases and the pacing interval of the anti-tachycardia pacing increases as the estimation of the action potential duration increases.

5. The method of claim 1, wherein detecting the tachycardia within the heart includes detecting the tachycardia within the atrium of the heart.

6. A method, comprising:
   detecting a tachycardia within a heart;
   applying anti-tachycardia pacing pulses to the heart;
   setting a pacing interval of the anti-tachycardia pacing pulses based on an estimate of action potential duration within the heart during application of the anti-tachycardia pacing pulses; and
   detecting P-waves within an atrium of the heart, wherein setting a pacing interval of the anti-tachycardia pacing pulses based on an estimate of action potential duration includes estimating the action potential duration based on a time interval between detected P-waves.

7. A method comprising:
   detecting a tachycardia within a heart;
   applying anti-tachycardia pacing pulses to the heart; setting a pacing interval of the anti-tachycardia pacing pulses based on an estimate of action potential duration within the heart during application of the anti-tachycardia pacing pulses; and
   detecting R-waves within a ventricle of the heart, wherein setting a pacing interval of the anti-tachycardia pacing pulses based on an estimate of action potential duration includes estimating the action potential duration based on a time interval between detected R-waves, and wherein detecting the tachycardia within the heart includes detecting the tachycardia within the ventricle of the heart.

8. The method of claim 5, wherein applying anti-tachycardia pacing pulses to the heart includes applying anti-tachycardia pacing pulses to the atrium of the heart.

9. The method of claim 7, wherein applying anti-tachycardia pacing pulses to the heart includes applying anti-tachycardia pacing pulses to the ventricle of the heart.

10. A device comprising:
    at least one electrode to detect electrical activity associated with a tachycardia; and
    a processor that determines an estimate of action potential duration and sets a pacing interval of anti-tachycardia pacing pulses based on the estimate of action potential duration within a heart at a time of application of the anti-tachycardia pacing pulses, wherein a processor that sets a pacing interval of anti-tachycardia pacing pulses based on the estimate of action potential duration includes a processor that detects a tachycardia in response to the detected electrical activity and estimates the action potential duration based on heart rate over a period of time prior to the detection of the tachycardia.

11. The device of claim 10, wherein the at least one electrode to detect electrical activity associated with a tachycardia includes an electrode to detect tachycardia in an atrium of the heart.

12. The device of claim 11, wherein the processor is configured to calculate the estimate of action potential duration as a function of an interval between P-waves signals as detected by the electrode.

13. The device of claim 10, wherein the at least one electrode to detect electrical activity associated with a tachycardia includes an electrode to detect tachycardia in a ventricle of the heart.

14. The device of claim 13, wherein the processor is configured to calculate the estimate of action potential duration as a function of an interval between R-waves signals as detected by the electrode.

15. The device of claim 10, further comprising a T-wave detection module to detect T-waves within the heart, wherein the processor is configured to calculate the estimate of action potential duration as a function of the T-waves signals received by the processor from the T-wave detection module.

16. The device of claim 10, further comprising memory to store heart rate over the period of time.

17. The device of claim 16, wherein the memory to store heart rate over the period of time includes a heart rate prior to detection of the tachycardia and a heart rate following the detection of the tachycardia.

18. The device of claim 16, wherein the processor further determines an effective diastolic interval based on the heart rate over a period of time and the memory further stores the diastolic interval as a state variable.

19. The device of claim 16, wherein the memory further stores the estimate of action potential duration, a diastolic interval, and an anti-tachycardia pacing therapy parameter.

20. The device of claim 10, wherein a processor that determines an estimate of action potential duration determines a first estimate and the processor further determines a second estimate of action potential duration wherein, the processor sets the pacing interval of anti-tachycardia pacing based on the second estimate of action potential duration.

21. The device of claim 10, further comprising a pulse generator to apply anti-tachycardia pacing pulses to the heart via at least one electrode, wherein at least one of the electrodes is electrically coupled to the pulse generator.

22. A computer-readable medium comprising instructions for causing a programmable processor to:
    detect a tachycardia within a heart;
    estimate an action potential duration based on a heart rate over a period of time prior to the detection of the tachycardia;
    apply anti-tachycardia pacing pulses to the heart; and
    set a pacing interval of the anti-tachycardia pacing pulses based on the estimate of action potential duration within the heart during application of anti-tachycardia pacing pulses.

23. The medium of claim 22, wherein the instructions that cause the processor to estimate an action potential duration includes instructions that cause the processor to calculate the estimate of action potential duration as a function of an interval between P-waves signals.

24. The medium of claim 22, wherein the instructions that cause the processor to estimate an action potential duration includes instructions that cause the processor to calculate the estimate of action potential duration as a function of an interval between R-waves signals.

25. The medium of claim 22, wherein the instructions that cause the processor to estimate an action potential duration includes instructions that cause the processor to calculate the estimate of action potential duration as a function of T-waves signals.

26. The medium of claim 22, in which the instructions that cause a processor to estimate an action potential duration includes instruction to cause the processor to estimate a first action potential duration, wherein the instruction further cause the processor to estimate a second action potential duration and set the pacing interval of the anti-tachycardia pacing pulses based on the estimate of the second action potential duration within the heart at a time of application of anti-tachycardia pacing pulses.

* * * * *